(12) United States Patent
Lesh

(10) Patent No.: US 7,244,270 B2
(45) Date of Patent: Jul. 17, 2007

(54) SYSTEMS AND DEVICES FOR SOFT TISSUE AUGMENTATION

(75) Inventor: Michael D. Lesh, Mill Valley, CA (US)

(73) Assignee: Evera Medical, Foster City, CA (US)

(*) Notice: Subject to any disclaimer, the term of this patent is extended or adjusted under 35 U.S.C. 154(b) by 490 days.

(21) Appl. No.: 10/942,728

(22) Filed: Sep. 16, 2004

(65) Prior Publication Data

US 2006/0058735 A1 Mar. 16, 2006

(51) Int. Cl.
*A61F 2/06* (2006.01)
*A61M 5/303* (2006.01)

(52) U.S. Cl. .................. 623/1.11; 604/239; 604/272

(58) Field of Classification Search ...... 623/1.11–1.25, 623/23.72; 604/272, 239
See application file for complete search history.

(56) References Cited

U.S. PATENT DOCUMENTS

| 2,512,568 | A | * | 6/1950 | Saffir ............................ 604/239 |
| 3,293,663 | A | | 12/1966 | Cronin |
| 3,919,724 | A | | 11/1975 | Sanders et al. |
| 3,934,274 | A | | 1/1976 | Hartley, Jr. |
| 3,949,073 | A | | 4/1976 | Daniels et al. |
| 3,953,566 | A | | 4/1976 | Gore |
| 4,187,390 | A | | 2/1980 | Gore |
| 4,383,929 | A | | 5/1983 | Bertocchio |
| 4,395,806 | A | | 8/1983 | Wonder et al. |
| 4,517,979 | A | | 5/1985 | Pecenka |
| 4,543,088 | A | | 9/1985 | Bootman |
| 4,545,367 | A | | 10/1985 | Tucci |
| 4,592,755 | A | | 6/1986 | Penton et al. |
| 4,631,188 | A | | 12/1986 | Stoy et al. |
| 4,643,733 | A | | 2/1987 | Becker |
| 4,648,880 | A | | 3/1987 | Brauman |
| 4,664,655 | A | * | 5/1987 | Orentreich et al. .......... 604/232 |
| 4,738,657 | A | | 4/1988 | Hancock et al. |
| 4,820,303 | A | | 4/1989 | Brauman |
| 4,828,561 | A | | 5/1989 | Woodruff |
| 4,828,827 | A | | 5/1989 | Henderson et al. |

(Continued)

FOREIGN PATENT DOCUMENTS

EP 0322194 6/1989

(Continued)

OTHER PUBLICATIONS

*Review of Injectable Materials for Soft Tissue Augmentation*, Mark R. Homicz, M.D. et al., *Facial Plastic Surgery*, vol. 20, No. 1, 2004.

(Continued)

*Primary Examiner*—Suzette Gherbi
(74) *Attorney, Agent, or Firm*—Knobbe, Martens, Olson & Bear LLP

(57) ABSTRACT

Medical devices, systems and kits for filling tissue are disclosed. The device has a first configuration wherein the device can pass through a small catheter or needle placed in the tissue to be filled and a second configuration in which the device is expandable to a predetermined or customizable shape. In one application, the device is adapted to be placed into the skin to reduce facial wrinkles or augment facial features such as the lips. Kits and systems include multiple device sizes, filler tubes, and filler media.

32 Claims, 7 Drawing Sheets

U.S. PATENT DOCUMENTS

| | | | |
|---|---|---|---|
| 4,840,615 A | 6/1989 | Hancock | |
| 4,863,470 A | 9/1989 | Carter | |
| 4,908,029 A | 3/1990 | Bark | |
| 4,917,646 A | 4/1990 | Kieves | |
| 4,944,749 A | 7/1990 | Becker | |
| 4,955,907 A | 9/1990 | Ledergerber | |
| 4,963,150 A | 10/1990 | Brauman | |
| 4,966,478 A | 10/1990 | Kuo | |
| 4,969,901 A | 11/1990 | Binder | |
| 4,994,028 A | 2/1991 | Leonard et al. | |
| 5,007,929 A | 4/1991 | Quaid | |
| 5,019,101 A | 5/1991 | Purkait et al. | |
| 5,074,878 A | 12/1991 | Bark et al. | |
| 5,098,779 A | 3/1992 | Kranzler et al. | |
| 5,102,389 A | 4/1992 | Hauser | |
| 5,116,387 A | 5/1992 | Berg | |
| 5,123,905 A | 6/1992 | Kelman | |
| 5,141,508 A | 8/1992 | Bark et al. | |
| 5,181,921 A | 1/1993 | Makita et al. | |
| 5,188,558 A | 2/1993 | Barton et al. | |
| 5,213,574 A | 5/1993 | Tucker | |
| 5,273,532 A | 12/1993 | Niezink et al. | |
| 5,282,856 A | 2/1994 | Ledergerber | |
| 5,324,259 A | 6/1994 | Taylor et al. | |
| 5,376,117 A | 12/1994 | Pinckuk et al. | |
| 5,387,192 A | 2/1995 | Glantz | |
| 5,425,747 A | 6/1995 | Brotz | |
| 5,425,760 A | 6/1995 | Rosenberg | |
| 5,437,900 A | 8/1995 | Kuzowski | |
| 5,456,716 A | 10/1995 | Iversen et al. | |
| 5,461,781 A | 10/1995 | Zukoski | |
| 5,480,430 A | 1/1996 | Carlisle | |
| 5,496,345 A | 3/1996 | Kieturakis et al. | |
| 5,496,370 A | 3/1996 | Hamas | |
| 5,514,153 A | 5/1996 | Bonutti | |
| 5,545,220 A | 8/1996 | Andrews et al. | |
| 5,549,672 A | 8/1996 | Maddock et al. | |
| 5,558,641 A | 9/1996 | Glantz | |
| 5,558,829 A | 9/1996 | Petrick | |
| RE35,391 E | 12/1996 | Brauman | |
| 5,582,585 A | 12/1996 | Nash-Morgan | |
| 5,584,859 A | 12/1996 | Brotz | |
| 5,599,852 A * | 2/1997 | Scopelianos et al. | 523/105 |
| 5,607,477 A | 3/1997 | Schindler et al. | |
| 5,630,843 A | 5/1997 | Rosenberg | |
| 5,630,844 A | 5/1997 | Dogan et al. | |
| 5,632,777 A | 5/1997 | Petrick | |
| 5,633,001 A | 5/1997 | Agerup | |
| 5,643,783 A | 7/1997 | Olsen et al. | |
| 5,645,081 A | 7/1997 | Argenta et al. | |
| 5,645,558 A | 7/1997 | Horton | |
| 5,653,755 A | 8/1997 | Ledergerber | |
| 5,653,757 A | 8/1997 | Petrick | |
| 5,660,849 A | 8/1997 | Polson et al. | |
| 5,674,285 A | 10/1997 | Quaid | |
| 5,702,677 A | 12/1997 | Shimp et al. | |
| 5,725,507 A | 3/1998 | Petrick | |
| 5,728,752 A | 3/1998 | Scopelianos et al. | |
| 5,779,672 A | 7/1998 | Dormandy, Jr. | |
| 5,779,734 A | 7/1998 | Ledergerber | |
| 5,782,913 A | 7/1998 | Schindler et al. | |
| 5,798,096 A | 8/1998 | Pavlyk | |
| 5,824,081 A | 10/1998 | Knapp et al. | |
| 5,861,032 A | 1/1999 | Subramaniam | |
| 5,863,297 A | 1/1999 | Walter et al. | |
| 5,922,025 A | 7/1999 | Hubbard | |
| 5,931,855 A | 8/1999 | Bancke | |
| 5,935,164 A | 8/1999 | Iversen | |
| 5,935,362 A | 8/1999 | Petrick | |
| 5,941,910 A | 8/1999 | Schindler et al. | |
| 5,944,738 A | 8/1999 | Amplatz et al. | |
| D413,672 S | 9/1999 | Fogarty | |
| 5,957,939 A | 9/1999 | Heaven et al. | |
| 5,961,552 A | 10/1999 | Iversen et al. | |
| 5,964,261 A | 10/1999 | Neuenfeldt et al. | |
| 5,964,803 A | 10/1999 | Iversen | |
| 5,989,214 A | 11/1999 | Van de Wijdeven | |
| 5,989,216 A | 11/1999 | Johnson | |
| 5,997,574 A | 12/1999 | Hayes et al. | |
| 6,039,712 A | 3/2000 | Fogarty | |
| 6,053,899 A | 4/2000 | Slanda et al. | |
| 6,060,639 A | 5/2000 | Petrick | |
| 6,090,063 A | 7/2000 | Makower et al. | |
| 6,098,629 A | 8/2000 | Johnson et al. | |
| 6,146,418 A | 11/2000 | Berman | |
| 6,162,251 A | 12/2000 | Kredovski | |
| 6,171,298 B1 * | 1/2001 | Matsuura et al. | 604/891.1 |
| 6,187,043 B1 | 2/2001 | Ledergerber | |
| 6,214,045 B1 | 4/2001 | Corbitt, Jr. et al. | |
| 6,228,116 B1 | 5/2001 | Ledergerber | |
| 6,231,586 B1 | 5/2001 | Mariant | |
| 6,231,613 B1 | 5/2001 | Greff et al. | |
| 6,241,747 B1 | 6/2001 | Ruff | |
| 6,258,055 B1 | 7/2001 | McCrory et al. | |
| 6,261,316 B1 * | 7/2001 | Shaolian et al. | 623/1.11 |
| 6,261,323 B1 | 7/2001 | Neto | |
| 6,267,772 B1 | 7/2001 | Mulhauser et al. | |
| 6,270,517 B1 | 8/2001 | Brotz | |
| 6,277,150 B1 | 8/2001 | Crawley et al. | |
| 6,296,624 B1 * | 10/2001 | Gerber et al. | 604/164.11 |
| 6,299,590 B1 | 10/2001 | Lüscher et al. | |
| 6,312,405 B1 | 11/2001 | Meyer et al. | |
| 6,315,796 B1 | 11/2001 | Eaton | |
| 6,322,576 B1 | 11/2001 | Wallace et al. | |
| 6,379,329 B1 | 4/2002 | Naglreiter et al. | |
| 6,440,098 B1 | 8/2002 | Lüscher | |
| 6,451,052 B1 | 9/2002 | Burmeister et al. | |
| 6,458,119 B1 | 10/2002 | Berenstein | |
| 6,470,216 B1 | 10/2002 | Knowlton | |
| 6,478,656 B1 | 11/2002 | Khouri | |
| 6,478,809 B1 | 11/2002 | Brotz | |
| RE37,950 E | 12/2002 | Dunn et al. | |
| 6,530,896 B1 | 3/2003 | Elliott | |
| 6,537,242 B1 | 3/2003 | Palmer | |
| 6,544,287 B1 | 4/2003 | Johnson et al. | |
| 6,551,342 B1 | 4/2003 | Shen et al. | |
| 6,578,580 B2 | 6/2003 | Conrad et al. | |
| 6,585,748 B1 | 7/2003 | Jeffree | |
| 6,599,310 B2 | 7/2003 | Leung et al. | |
| 6,629,947 B1 | 10/2003 | Sahatjian et al. | |
| 6,648,853 B1 | 11/2003 | McEntee | |
| 6,660,301 B1 | 12/2003 | Vogel et al. | |
| 6,663,596 B2 | 12/2003 | Griego et al. | |
| 6,673,105 B1 | 1/2004 | Chen | |
| 6,684,107 B1 | 1/2004 | Binder | |
| 6,699,176 B1 | 3/2004 | Khouri | |
| 6,702,731 B2 | 3/2004 | Milbocker | |
| 6,716,251 B1 | 4/2004 | Asius et al. | |
| 6,725,866 B2 | 4/2004 | Johnson et al. | |
| 6,740,082 B2 | 5/2004 | Shadduck | |
| 6,743,208 B1 | 6/2004 | Coyle | |
| 6,878,137 B2 | 4/2005 | Benchetrit | |
| 6,921,418 B2 | 7/2005 | Ledergerber | |
| 7,094,230 B2 * | 8/2006 | Flaherty et al. | 604/891.1 |
| 2002/0019670 A1 | 2/2002 | Crawley et al. | |
| 2002/0022861 A1 | 2/2002 | Jacobs et al. | |
| 2002/0025340 A1 | 2/2002 | Dyer | |
| 2003/0028147 A1 * | 2/2003 | Aves et al. | 604/164.06 |
| 2003/0074021 A1 | 4/2003 | Morriss et al. | |
| 2003/0225453 A1 * | 12/2003 | Murch | 623/1.21 |
| 2004/0037887 A1 | 2/2004 | Bourne et al. | |
| 2005/0131325 A1 * | 6/2005 | Chen et al. | 602/41 |
| 2006/0058890 A1 | 3/2006 | Lesh | |
| 2006/0058891 A1 | 3/2006 | Lesh | |

| | | | |
|---|---|---|---|
| 2006/0058892 | A1 | 3/2006 | Lesh |
| 2006/0161253 | A1 | 7/2006 | Lesh |

FOREIGN PATENT DOCUMENTS

| | | |
|---|---|---|
| EP | 0357927 | 3/1990 |
| EP | 0411767 | 3/1991 |
| WO | WO 95/22359 | 8/1995 |
| WO | WO 99/17816 | 4/1999 |

OTHER PUBLICATIONS

*Collagen, Human Collagen, and Fat: The Search for a Three-Dimensional Soft Tissue Filler*, Anthony P. Sciafani et al, *Facial Plastic Surgery*, vol. 17, No. 1, 2001.

*Patient Satisfaction with Expanded Polytetrafluoroethylene (Softform) Implants to the Perioral Region*, Stephen J. Wall, M.D., Ph.D., et al., *Arch Facial Plast* Surg. vol. 5, Jul./Aug. 2003.

U.S. Appl. No. 11/575,493, filed Mar. 16, 2007, Lesh.

* cited by examiner

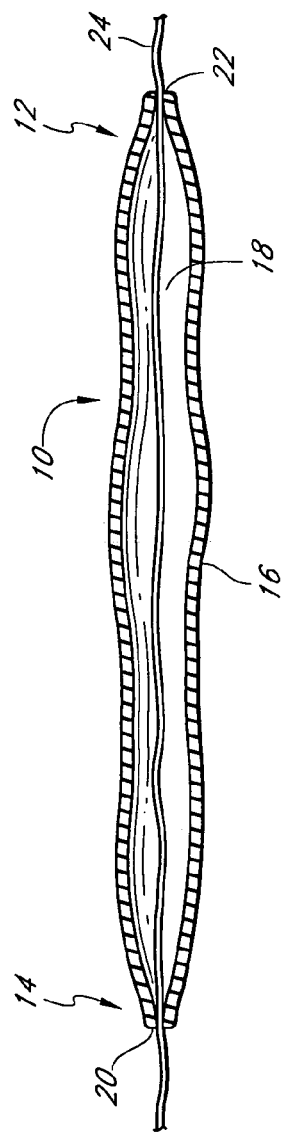
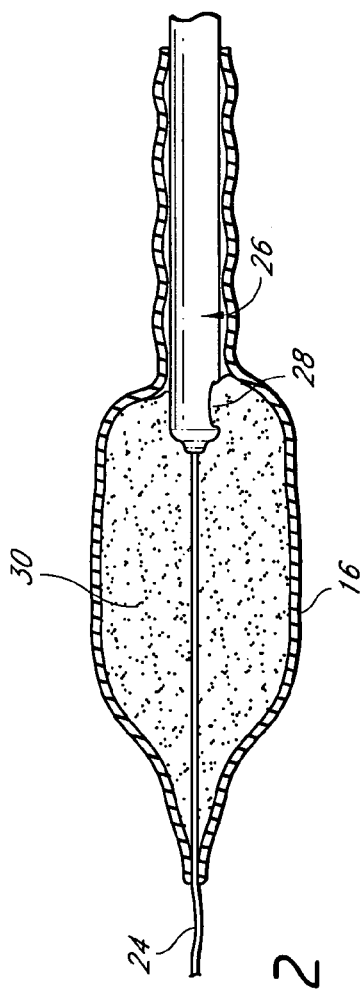
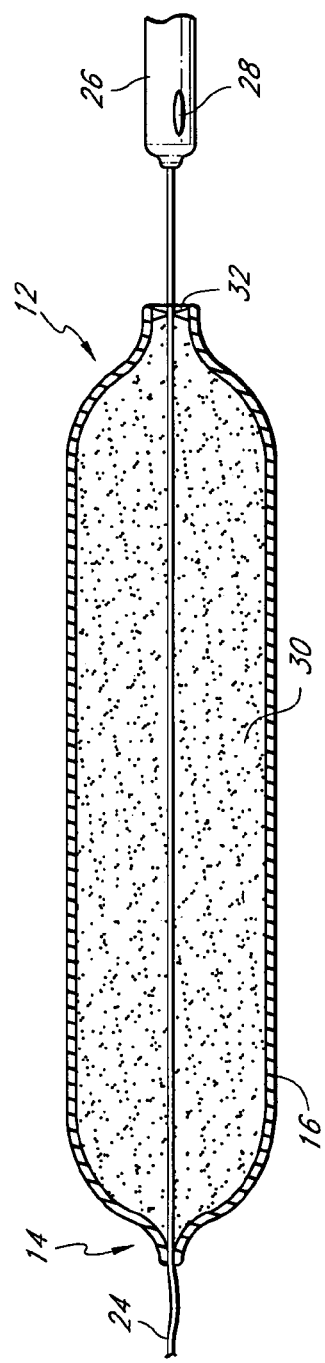

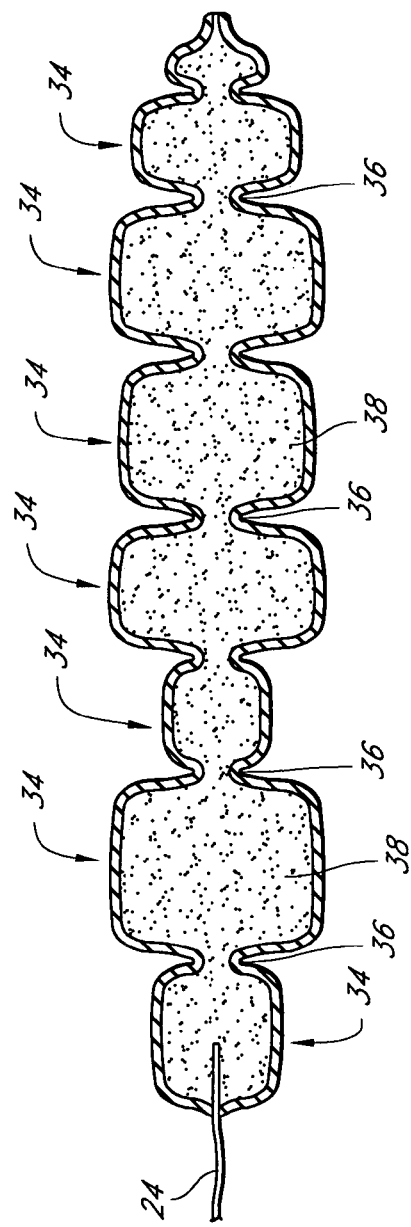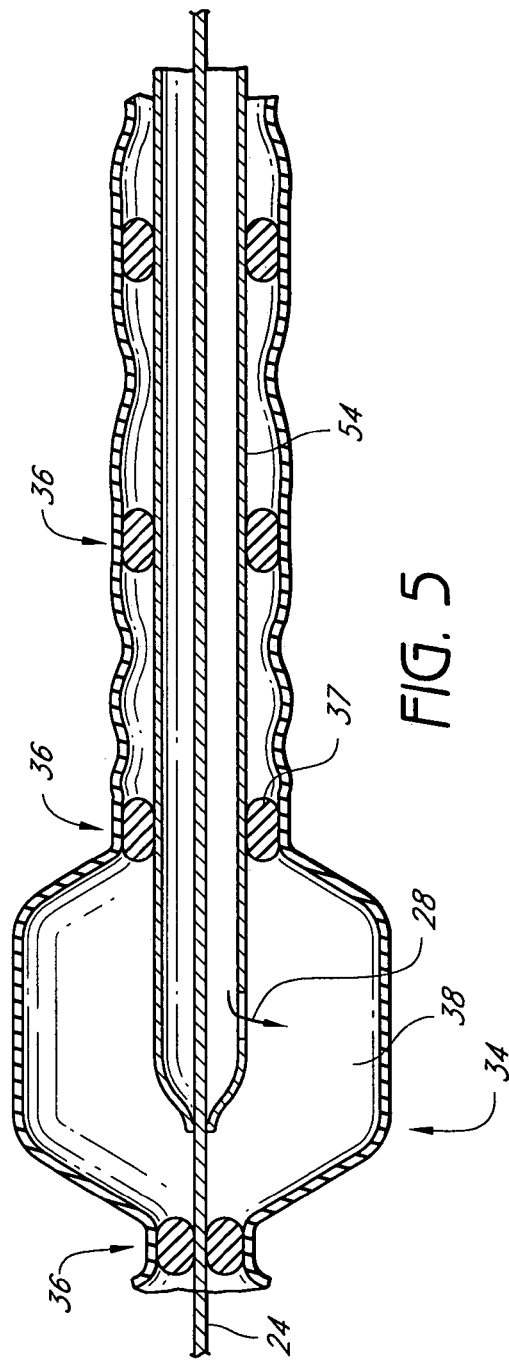

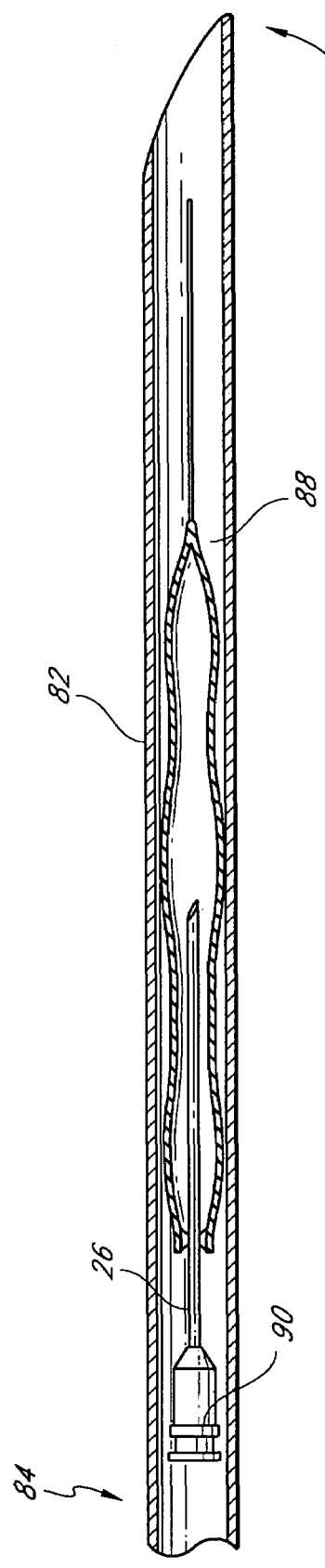
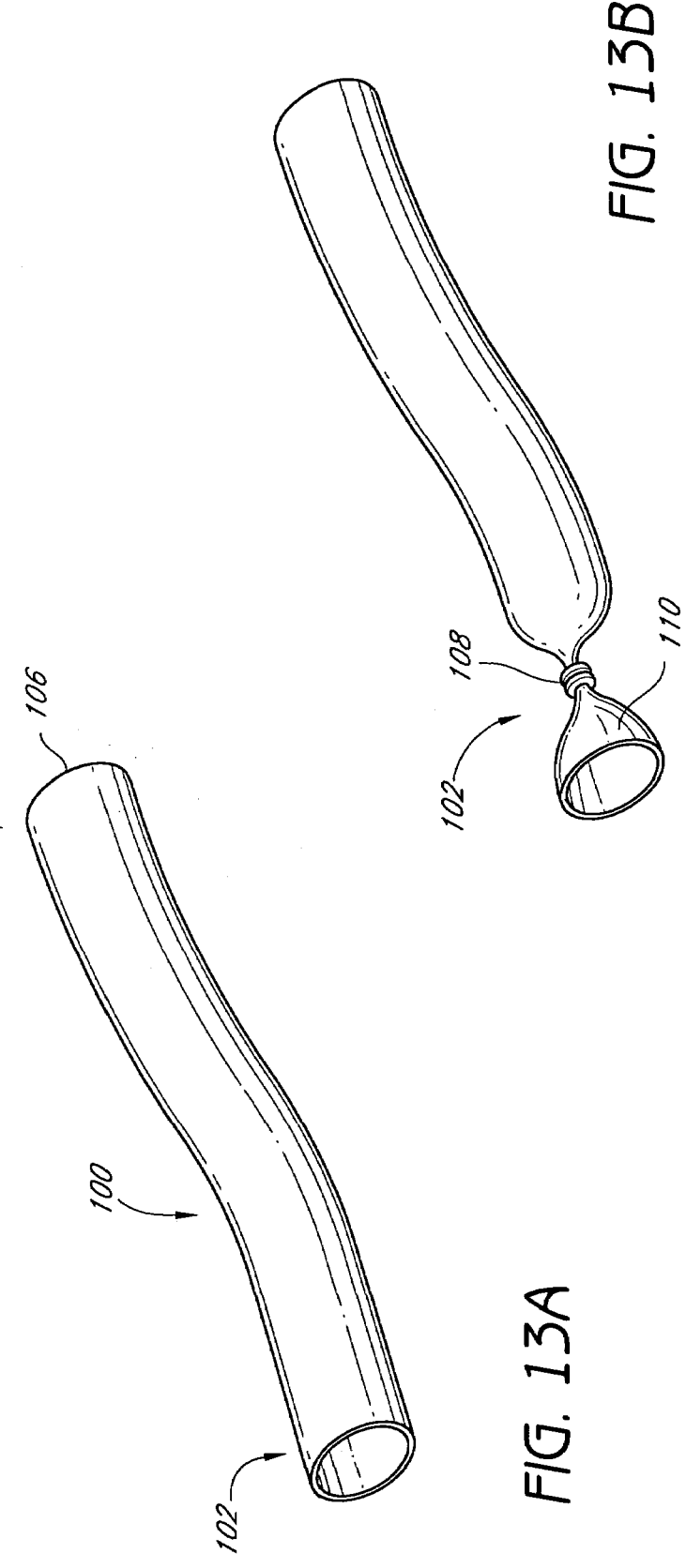

SYSTEMS AND DEVICES FOR SOFT TISSUE AUGMENTATION

BACKGROUND OF THE INVENTION

There is a growing demand for cosmetic procedures which augment soft tissue to enhance facial appearance. The American Society for Aesthetic Plastic Surgery reports nearly 8.3 million aesthetic procedures were performed in 2003, and increase of 20% from the year before. The most common of these procedures are intended to remove facial wrinkles and lines or augment the lips to restore a more youthful appearance.

Botulinum toxin is used to paralyze the small facial muscles around dynamic wrinkles in the forehead and around the eyes. Materials that have been used to smooth non-dynamic wrinkles or augment facial tissues (nasolabial lines, lips, etc.) include injectable soft tissue fillers such as silicone, collagen in a variety of forms and formulations such as Inamed Corporation's CosmoDerm and CosmoPlast, hyaluronic acid derivatives such as Restylene and Hyaloform, and calcium hydroxylapatite microspheres such as Radiance. Autologous fat can also be taken from a donor site by liposuction and then injected in the targeted facial tissue. While these injectable fillers are convenient, and some can even be done as a simple office procedure, the results are temporary and once injected, the filler cannot be removed.

Implanted artificial tissue fillers are well known and are generally placed through surgical incisions. These include ePTFE-based tubes, fibers or sheets, including Gore Subcutaneous Augmentation Material (S.A.M.), Advanta, marketed by Atrium Medical, and Ultrasoft and Softform marketed by Tissue Technologies, now Integra Life Sciences. Surgically implanted tissue fillers can also be derived from biologic sources such as Alloderm from LifeCell Corp. and DuraDerm from Collagensis, Inc.

Surgically implanted fillers have a number of limitations such as prolonged recovery time due to bruising and swelling which is unacceptable to many patients, risk of infection or granuloma formation, erosion, shrinking and migration. Many patients cannot accept the fact the implant is palpable under the skin because it is firmer than the surrounding skin. The implanted fillers may also be difficult to remove, should the patient wish, or a complication arises that demands its removal.

The ideal facial tissue filler would be: completely biocompatible; easy to place through a relatively small needle, as opposed to through a surgical incision; would be permanent but could be removed either at the time of the procedure to allow for re-positioning, or at some time in the future; would have a very low risk of infection or immunologic response; would not expand, contact or migrate over time; would not erode; and would not be noticeable to the patient.

Biocompatible medical devices that have a small enough profile to fit into a catheter, yet self-expand or are made to expand when such a device is released from the distal end of the catheter, are ubiquitous in vascular, cardiovascular and neurovascular intervention. Such devices include various types and configurations of self-expanding or balloon expandable stents, and embolization coils. These devices are often constructed of a metal and can be covered with a polymer such as a sleeve of e-PTFE.

However, there remains a need for a device of a similar nature that can be placed within a non-vascular space such as dermal tissue, which can be enlarged in situ to provide a desired cosmetic or therapeutic result.

SUMMARY OF THE INVENTION

There is provided in accordance with one aspect of the present invention, a tissue augmentation system. The system comprises a tubular channel adapted to be placed within human tissue, and a tissue dilator adapted to pass through the tubular channel. A tissue filling device is provided, having a first configuration and a second configuration. The first configuration is adapted to fit through the tubular channel and the second configuration is formed to fill the tissue. The device is transformable from the first configuration to the second configuration upon introduction of a filler into the device after the device has been delivered into the tissue through the tubular channel.

The tubular channel may be a needle, catheter, cannula, or other access device. The tissue to be augmented may be the skin.

In accordance with another aspect of the present invention, there is provided a tissue augmentation device. The device comprises an elongate flexible body, having a proximal end and a distal end. At least a first port is provided on the proximal end, for accessing the interior of the body. A suture extends from the distal end.

A needle may be provided on the suture, for percutaneous access to a treatment site. The body may comprise a tubular sleeve, which may have a circular or flattened cross section. The body may comprise two sheets of material bound together along a periphery. The body may also comprise two concentric tubular layers. At least a second port may be provided, for accessing the interior of the body. One or more valves may be provided, for closing the port. In certain embodiments, at least two compartments may be provided within the flexible body.

In accordance with a further aspect of the present invention, there is provided a kit for augmenting tissue. The kit comprises at least one elongate flexible body, which is transformable from a first configuration for implantation to a second configuration for augmentation. At least one suture is attached to the body. A filler tube is provided, for permitting access to the interior of the body. A filler is additionally provided, for transforming the body from the first configuration to the second configuration.

The body may comprise a tubular sleeve, which may have one or a plurality of internal compartments. The body may additionally comprise a valve. At least a second suture may additionally be attached to the body. The filler may comprise a liquid, and may be polymerizable in situ. The kit may additionally comprise a syringe, for injecting the filler into the filler tube.

In accordance with a further aspect of the present invention, there is provided a kit for augmenting tissue. The kit comprises a plurality of elongate flexible bodies, each of which is transformable from a first configuration for implantation to a second configuration for augmentation, provided in a plurality of sizes and shapes. At least one suture is attached to each body. A deployment tube is provided, for delivering the body to a treatment site. A filler tube is provided for permitting access to the interior of the body, and a filler is provided, for transforming the body from the first configuration to the second configuration.

In accordance with another aspect of the present invention, there is provided a kit for augmenting tissue. The kit comprises a plurality of elongate flexible bodies, each of which is transformable from a first configuration for implantation to a second configuration for augmentation. The flexible bodies are provided in a plurality of sizes and shapes. At least one suture is attached to each body. A filler tube is provided for permitting access to the interior of the body, and at least two different fillers for transforming the body from the first configuration to the second configuration are also provided. The fillers may have different viscosities, and/or different durometers.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a schematic side elevational cross section through an empty sleeve in accordance with the present invention.

FIG. 2 is a side elevational cross sectional view through a partially inflated sleeve.

FIG. 3 is a side elevational cross sectional view through a filled sleeve having a uniform exterior profile.

FIG. 4 is a cross sectional side elevational view through a segmented sleeve, having customized fill volumes in each segment.

FIG. 5 is a cross sectional view through the distal end of an implant, illustrating a filler tube in position to fill a single segment.

FIG. 12 is a side elevational schematic view of an implant and filler tube assembly, positioned within a delivery cannula.

FIG. 13A through 13D illustrate an assembly sequence for a soft tissue bulking device in accordance with the present invention.

DETAILED DESCRIPTION OF THE PREFERRED EMBODIMENT

Figure 6:
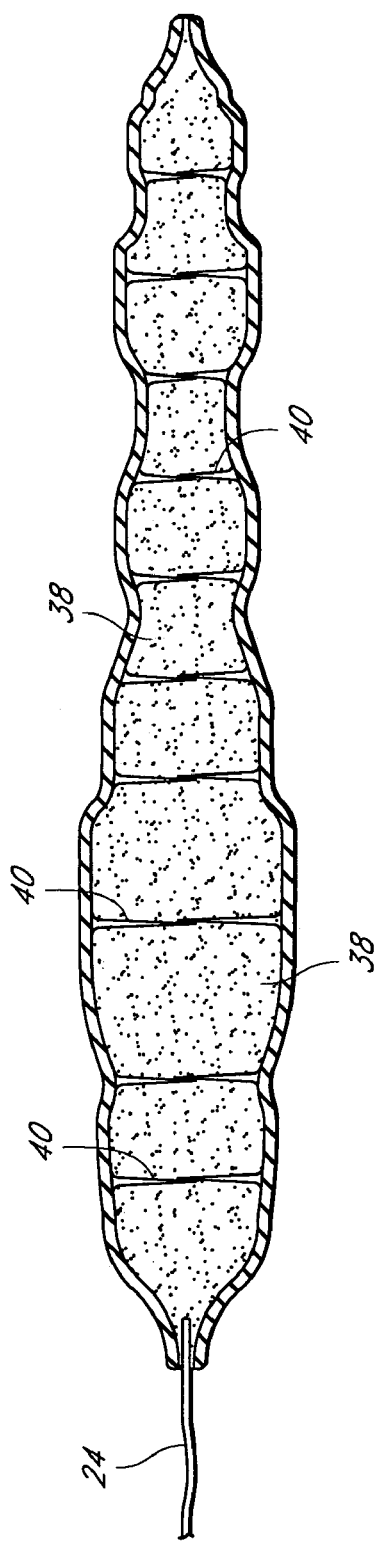
FIG. 6 is a side elevational cross sectional view through a segmented sleeve having a plurality of internal baffles.

The invention is, generally, a system and method for volume augmentation of tissue in a living being, preferably, a human. The system consists generally of a tissue-filling device and a method for delivering said tissue-filling device into tissue. The tissue-filling device consists of tissue filler material and an enclosing sheath. Preferably, the enclosing sheath forms a container that is filled.

The volume augmentation methods and devices described in the present patent are intended to be used for tissue bulking in a variety of circumstances, depending on the need. For example: in gastroenterology, wherein increasing the volume of tissue at the gastro-esophageal junction can be used to treat gastro-esophageal reflux disease, and increasing the thickness of the gastric mucosa to decrease the volume of the stomach to treat morbid obesity; in urology, where placing filler radially around the urethra at the neck of the urinary bladder can ameliorate incontinence; and in cardiology, whereby tissue filler may be placed in the ventricular wall to decrease the volume of the left ventricular chamber to treat heart failure, or in the pericardial space to place pressure on the outside of the heart, also intended to decrease the volume of the heart chambers and thereby treat heart failure; and in other applications well known to those skilled in the art. In any of these clinical applications, the tissue-filling device may be combined with any number of other bioactive substances which may be released from the filler itself over time, or be injected concurrently.

One preferred use of the present invention is in the field of cosmetic plastic surgery wherein the system is used for augmentation in the dermis or subdermis to treat skin contour deficiencies caused by various conditions, including aging, environmental exposure, weight loss, child bearing, surgery, disease such as acne and cancer, or combinations thereof, or for beauty enhancement. The tissue augmentation method of the present invention is particularly suitable for treating frown lines, worry lines, wrinkles, crow's feet, facial scars, or marionette lines, or to augment facial features such as the lips, cheeks, chin, nose or under the eyes. Treatment of a patient may consist solely of using a tissue-filing device, or the tissue-filling device may be used as part of additional cosmetic surgery such as a face or brow lift. The characteristic of change from first configuration to second configuration makes the tissue-filling device desirable for use in endoscopic surgery. The tissue augmentation device may also be used for breast augmentation, and regions of the body that need volume enlargement during reconstructive plastic surgery, such as after trauma or tumor resection.

The sleeve can be embodied as a variety of structures, and constructed of a variety of materials. The term "sleeve" as used herein is meant to include any structure adapted to substantially separate a filler material from the tissue in which the tissue-filling device is implanted. The term "skin" and "membrane" is used interchangeably and has the same scope of meaning as sleeve.

In one embodiment, a sleeve is placed in the tissue to be filled, and as a second step, the sleeve is filled with material such that the sleeve, when filled, creates a volume adequate to alter the tissue contour as required to produce the clinical result. Filling can either be accomplished through the device used to implant the sleeve, or through a separate device, or both, as will be discussed. In an alternative embodiment, the tissue-filling device is constructed prior to its implantation in the tissue by filling a sleeve with a tissue filler and the assembled tissue-filling device is placed in the tissue. In still another alternative embodiment, the tissue filler may be of more than one component such that one (or more) component of the tissue filler is in place inside the sleeve before the sleeve is placed in the tissue to be augmented, and a second component (or components) are placed within the sleeve after the sleeve has been placed in the tissue, the combination of the components than constituting the final filler material.

The sleeve can be compliant or non-compliant, or a combination of compliant and non-compliant components. The sleeve may be made of a biocompatible but non-biodegradable material. Suitable materials include e-PTFE, PTFE, polypropylene, polyacrylamide, polyurethane, silicone, polymethylmethacrolate, Dacron, metals tubes or meshes of nickel titanium alloys such as Nitinol, silver, gold, platinum, or stainless steel. The sleeve can consist of a plurality of layers of materials. Other biocompatible materials are well known in the art, as, for example, disclosed in U.S. Pat. No. 5,630,844 to Dogan, the disclosure of which is incorporated by reference in its entirety herein.

If fibrous tissue ingrowth is desired, then the sleeve can be made of or covered with ePTFE with a pore size of in the range of from about 40 to about 100 μ. If the filler material is, or becomes, non-flowable, the sleeve may be made of a biocompatible and biodegradable material chosen from any of various polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher polymonomer polymers thereof or combinations or mixtures thereof, such that the initial implantation of the filler device consists of a sleeve and filler material, but over time, the sleeve is resorbed and only the filler material is left behind to augment the tissue.

In one embodiment, the sleeve consists of an outer layer of ePTFE of about 40 to 100 μ pore size and about 0.001 to 0.010 in thickness to encourage fibrous tissue ingrowth, and an inner sleeve of polyethylene or similar material of about 0.001 to 0.010 in thickness to add flexibility to the sleeve and to more completely contain the filler material. Such double layer structure is particularly suited where the ePTFE is permeable or semipermeable to the filler material, such as when the filler material is, or contains a component of, water.

The sleeve may contain, or be contained by, a skeletal structure such as struts of a metal including alloys such as nitinol, stainless steel, gold, or platinum, a polymer such as PLA or PLG, or any material of sufficient durometer or structural integrity to provide support of the sleeve or to provide for a three-dimensional shape. Struts can extend in an axial direction, a circumferential direction or both depending upon the desired clinical performance. Additionally, the struts may have anchor elements or hooks which extend through the sleeve, adapted to stabilize the tissue-filling device within the tissue.

In one embodiment, the sleeve itself is high flexible. Therefore, the material should be thin, such as within the range of from about 0.001" to about 0.010". The sleeve may be manufactured to be of fixed length and shape, with a plurality of lengths and shapes provided in a kit, depending on the need to fill a specific region of tissue in a particular patient, or the sleeve may be cut to size at the clinical site as a part of the implantation procedure. For a given region to be filled, more than one tissue filling device may be placed to achieve a given desired contour. In one embodiment, a plurality of sleeves are provided that are bound together to create a bundle.

The tissue-filling device may be provided in a kit which includes one or more sleeves, and one or more filler materials. Or the sleeve may be supplied separately in a kit, and another kit includes one or more filler materials. Or the kit may consist solely of one or more sleeves, and the surgeon provides the filler material from an alternate source.

The sleeve may have a constant inflated diameter, generally 1-10 mm, or it may have an inflated diameter that varies along its length depending on the desired contour of the augmented tissue. For glabellar folds, the inflated diameter is, preferably, 0.5 to 2 mm. For lips, the inflated diameter is, preferably, 1.5 to 2 mm. For the upper lip, the inflated diameter preferably varies along its length adapted to form the "m" shape of the upper lip. For the lower lip, the sleeve generally tapers at the proximal and distal end, with a larger diameter of 2 to 8 mm at the central portion. In addition, for the lower lip, the profile of the sleeve will be generally a flattened "u" shape adapted to follow the profile of the lower lip. For nasolabial folds, the inflated diameter is, preferably, 2 to 6 mm, with tapering at the proximal and distal ends. In one embodiment, the sleeve comprises a series of segments such that the internal diameter of each segment is greater than the internal diameter of that portion of the lumen between segments. Further, the sleeve may have internal segmentation embodied by a series of valves or baffles. In the case of a segmented sleeve, each segment may be filled with a different volume of filler material in order to create a profile customized along the axial length of the implant to suit the specific clinical need. The sleeve may have supporting struts, such as a skeleton made from filaments, where said filaments may be composed of any biocompatible material adapted to provide structure.

A valve, or a plurality of valves, can be affixed to one or both ends of the sleeve, or along any portion of the wall of the sleeve, in order to prevent filler material from escaping into the surrounding tissue. The required integrity of the valve is dependent on the type and viscosity of the filler material. For example, if the filler material gels in place, or the filler is composed of beads of sufficient size, then the valve may not need to close tightly. In one embodiment, the valve is one or more elastomeric bands that encircles the proximal end of the sheath. In another, the valve is one or more elastomeric bands placed, during construction of the tissue filling device, 1 to 4 mm, distal from the proximal end of the sheath, and then when the sheath is turned inside out during its construction, the valve is placed on the interior portion of the sleeve, enhancing the ability of the valve to remain closed as the sleeve is filled with filler material. In another, the valve is a band of nitinol adapted to form a spring closure at the proximal end of the sheath. Other valves known in the art include, for example, U.S. Pat. No. 5,779,672 to Dormandy or U.S. Pat. No. 6,102,891 to van Erp, the disclosures of which are incorporated by reference in their entireties herein. In addition to valve placement at the proximal end of the sheath, valves may be deployed at a plurality of locations within the sheath to form segments, which then allows individual segments to be filled with different amounts of filler material.

The filler material can be any of a number of biocompatible substances and may be of various physical states or combinations thereof, such as a non-viscous liquid, a viscous liquid, a gel, a powder, beads, flakes, continuous or discontinuous fibers, coils, fiber balls or mixtures thereof. The filler material may be transformable from a first state to permit introduction into the sheath, to a second state once inside the sheath. Combinations, such as a fiber carried within a liquid or gel are well within the contemplated scope. For example, the filler can consist of a substantially linear filament which itself can be made of a variety of materials such as nitinol, various biocompatible polymers well known to those skilled in the art, e-PTFE, Proline or any biocompatible material with adequate strength to alter the contour of the tissue in which it is injected. The filler material may consist of any of a number of materials commercially available and sold as tissue fillers, such as Zyplast™, available from Inamed Aesthetics; Restylane™, available from Q-Med and Genzyme, Inc.; HylaforM™, available from Inamed Aesthetics; Artecoll™ available from Artes, Inc.; Radiance™ available from Bioform, Inc.; or Sculptura™ PLA filler available from Aventis, Inc.

Other embodiments of the filler material include a flexible random or regular coil; knit fibers; woven fabric; a series of filaments wound around each other, a compressible or non-compressible sponge material, a closed or open cell foam, or any others depending on the specific need as is well known to those skilled in the art. The filler material could be a set of objects connected with a outer membrane or an axial filament, or could be a series of discrete objects. If it is desired that the tissue-filling device be visible by x-ray or fluoroscopic imaging, then radio-opaque coatings such as triazoate, barium salts or tantalum can be included in the filler material. If ultrasonic visualization is required, small trapped air bubbles or other echocontrast material can be included in the filler material. The filler material may contain a colored dye in order to render the tissue filling device less visible from outside the tissue.

One class of fillers comprises a mix of solid particles and a carrier. One solid particle comprises micronized particles of e-PTFE. Other materials that are suitable for use in the present invention include, but are not limited to, PDS II (polydioxanone, a monofilament), Nurolon (a long chain aliphatic polymer Nylon 6 or Nylon 6, 6) Ethilon (a long chain aliphatic polymer Nylon 6 and Nylon 6, 6), Prolene (Polypropylene, isotactic crystalline stereoisomer of polypropylene, a synthetic linear polyolefin.), Victyl (co-polymer made from 90% glycolide and 10% L-lactide), silk, Monacryl (poly .epsilon.-caprolactone.), polylactide, polyglycolide, poly lactide-co-glycolide, Medpor (biocompatible (micronized) polyethylene), BIOGLASS (bioactive glass particulate), or polyhydroxyvalerate.

Carriers that may be suitable for use in the present invention either alone, as a filler, or in combination with particles include, but are not limited to, polyvinylpyrrolidone (PVP), silicone oil, vegetable oil, saline, gelatin, collagen, autologous fat, hyaluronic acid, autologous plasma, $CO_2$ or other gas, and other physiological carriers.

Another class of fillers includes liquids, gas or gels without discrete solid particles. For example, PVP may be used alone or in combination with other agents. PVP is a water-soluble polyamide that possesses unusual complexing and colloidal properties and is physiologically inert. PVP is commercially available as a biocompatible gel that is freely transported through the body and is excreted unchanged by the kidneys. This gel has trade names such as Au24k and Plasdone C-15 and Plasdone C-30, and consists of macromolecules from the plasdone family, having the empirical formula $(CHCH.sub.2).sub.2N(CH.sub.2).sub.3$— —CO. Polymers of this family have been used as binders, extenders, and vehicles for a variety of medications for nearly fifty years, and would be expected to be well tolerated and quickly removed from the body in the event of a valve failure, if the sleeve were to rupture or leak, or if material were mistakenly injected into the tissue, rather than into the sleeve, during the implantation procedure.

PVP is available commercially in many molecular weight ranges and is polymerized to have an average molecular weight in a particular solution. For example, PVP is available in solutions of an average molecular weight of 10,000 daltons, 40,000 daltons and 360,000 daltons. Preferably, the PVP is less than about 60,000 daltons to allow for easier renal excretion. PVP is also defined by its viscosity measurement, or K value. K values range from approximately less than 12 to 100. PVP compositions which may be desirable with the present invention are within a range of K values of from about 12 to 50. PVP is commercially available from International Specialty Products, Inc., GAF Chemical Corp., Wayne, N.J., USA, and from BASF Aktiengesellschaft, Germany. In use, the gel polymer may be diluted with deionized water or saline to produce the desired viscosity, is sterilized, and placed in cartridges for injection. Alternatively, the dehydrated polymer particles may be placed within the sleeve prior to its being placed in the tissue to be augmented, and sterile saline added after the sleeve has been placed, resulting in gel formation within the sleeve, and thence expansion of the tissue. Alternatively, the dehydrated polymer particles may be supplied in a sterile container and reconstituted with saline or water just prior to filling the sleeve.

Once the filler material is inside the sleeve, its material state or chemical structure may be altered via a number of mechanisms, such as the addition of a second material acting as a catalyst, heat or cold, change in pH, ultrasound or light, or the state change may happen spontaneously over a period of time. If the material changes its state over time, that time would ideally be in the range of 10 to 30 minutes from injection so that the clinician can mold the shape by manual palpation to a desired configuration before the filler transforms to retain its molded configuration. Alternatively, the state change would take place over 24 to 48 hours so the patient can sculpt his or her own filler configuration. In one embodiment, the filler material is a biocompatible polymer which fills the sleeve in a relatively flowable state, is molded from the skin surface by the operator to the desired shape, then light of the appropriate wave length (e.g., UV) is directed at the skin in order to convert the liquid to a non-flowable gel, which gel retains the desired suppleness. In one embodiment, the gel consists of a backbone of PEG and/or PVA, with PLA and/or PLG side groups attached to allow for biodegradability of any gel which fails to fill the sleeve or leaks out, and methylacrylates subunits attached to the backbone to induce photopolymerization with light of wavelength about 400-500 nm.

The filler material may be capable of reversing its state change, via any of the mechanisms describe above, to allow for subsequent removal of the filler material by aspiration via a channel placed in the sleeve from outside the tissue. In one embodiment, the channel is a needle which contains or is surrounded by an ultrasound crystal such that when the needle is inserted into the sleeve and energy is supplied to the ultrasound crystal, causing it to vibrate in the range of 100 khz to 1 megahertz, the gelled filler material is broken down into a flowable material allowing for aspiration through the needle.

In another embodiment, the filler material consist a purified protein such as available from Gel-Del Technologies and described in U.S. Pat. No. 6,342,250 and U.S. patent applications Ser. Nos. 20030007991, 20020106410, and 20020028243, 875 the disclosures of which are incorporated by reference in their entireties herein, which turns into a gel at body temperature and can be changed back into a flowable liquid by application of cold.

In another implementation of the invention, the tissue filling device consists of a sheath and a volume of internal foam. In this embodiment, a valve may not be required, since the foam structure itself acts to prevent filler from escaping from the sleeve. The foam may be a structure having an open or closed cell configuration. In one embodiment, the foam is a closed cell elastomer that is highly compliant, and the sheath is one of the materials noted above. The foam may be biocompatible polyurethane. The sheath may be ePTFE which is bonded to the outside of the foam. In use, the tissue filling device is placed in the tissue either directly or via the pull through sewing method previously described. Once in place, the tissue filling device is injected from a site or sites externally to the tissue to be filled, such as from the surface of the skin, with a fluid, such as water, saline, silicone, a hydrogel, or any of the filler materials described above including combinations of solid or gel particles or filaments within the fluid carrier. Preferably, a small hollow structure is used to inject the filler material, such as a 25-32 guage hypo-tube or needle. This results in local enlargement of the tissue filling device as the closed cell foam is filled in the region in which the filler is injected. Additional sites along the tissue filling device are injected in order to customize the shape of the augmentation. If too much filler has been injected in a region, filler can be removed by re-entering the region that needs to be shrunk, and then withdrawing filler. The entry of the hypo-tube or needle into the region that needs to be shrunk can be via the same route through which the region was filled, or another pathway may be taken, such as through the skin generally perpendicularly to the axis of filling. Alternatively, additional filler material can be added during the procedure, or at any later time as desired.

The foam body is thus constructed of a cellular foam matrix having a multiplicity of cells which divide the interior volume of the implant into compartments numbering from 100 to 1,000,000 depending on the filler material chosen and the desired feel of the filled tissue. The cellular foam material may be a thermoset or thermoplastic polymer. Preferably, the cellular foam material has elastomeric qualities but may be of a non-elastomeric polymer foam. The shape of the foam body influences the basic range of shapes of the implant and for many wrinkle applications will be an elongate body having in an uninflated configuration a length of at least about 5 times and often at least about 20 times its average un-inflated cross section. The particular material or materials chosen for constructing the foam body will depend, at least in part, on the density or hardness of the tissue to be simulated.

In certain implementations, the foam body may have an "open-cell" structure, the cells being interconnected with one another by passages that permit intercellular communication of the fluid filler. The passages interconnecting the cells 20 allow the flow of fluid filler from cell to cell, which may create a hydraulic cushioning effect upon localized deformation of the implant by external pressure. The hydraulic cushioning effect created by intercellular fluid communication may help to impart realistic shape and tissue-like consistency to the implant. The viscosity of the filler at body temperature is preferably related to the passage size to inhibit excessive free flow between cells in the absence of external pressure.

The foam body may have a uniform cellular density throughout, or may have a cellular density that varies throughout one or more regions, i.e., a cellular density gradient. In the case of an embodiment that includes one or more regions 30, 32 having a cellular density gradient, the regions 30, 32 will have different average cellular densities. The average cellular density of a region can be selected to cooperate with the viscosity of the filler to influence the response of the implant to external pressure.

In another embodiment, the open cell structure may be placed within a courser closed cell structure, such that the open cell foam is compartmentalized into regions such that filler remains in a given region, and each region may be filled separately in order to vary the contour of the filled region.

The sleeve for the foam filled embodiment may comprise any of the materials identified previously, as well as linear aliphatic polyether urethane; linear aliphatic polyester urethane; cyclic aliphatic polyether urethane; cyclic aliphatic polyester urethane; aromatic polyether urethane; aromatic polyester urethane; polybutylene; polypropylene; crosslinked olefinic elastomers; styrene-ethylene/butylene-styrene block copolymer; or any other biocompatible material which is substantially radiolucent under standard mammographic or other imaging protocols and intensities. The fluid filler may comprise a biocompatible triglyceride, serum, saline solution, or another biocompatible material which is substantially radiolucent under standard mammographic protocols and intensities.

The foam body may also be made of a material which is substantially radiolucent under standard mammographic or other imaging protocols and intensities. The foam body may be constructed of styrene-ethylene-butylene-styrene copolymer; polyethylene; polyurethane; and polytetrafluoro-ethylene; or another biocompatible material which is substantially radiolucent under standard mammographic or other imaging protocols and intensities.

Coatings can be applied to all or a portion of any of the sleeves disclosed herein, either on the outside or the inside thereof. Methods of applying coatings to biocompatible substances are well known in the art. See, for example, U.S. Pat. Nos. 6,660,301 to Vogel, 6,368,658, and 6,042,875 the disclosures of which are incorporated by reference in their entireties herein. The formation of and coating with hydrogels is disclosed in U.S. Pat. No. 6,652,883 to Goupil the disclosure of which is incorporated by reference in its entirety herein. Coatings that make the sheath sticky such as fibronectin or vitronectin or laminin can be used if desired to inhibit movement of the sheath relative to the tissue. If it is desired that the sheath be visible by x-ray or fluoroscopic imaging, then radio-opaque coatings such as triazoate, barium salts or tantalum can be used on the sheath.

Coatings can also be applied with a biologically active or therapeutic effect, as needed in the clinical application. For example, growth factors such as fibroblast growth factor, anti-inflammatory agents such as corticosteroids to reduce the amount of fibrosis, antibiotics to reduce the risk of infection on the implant, and anesthetics such as lidocaine, procaine or marcaine to decrease pain. In order to modulate fibroblast proliferation, TNP-470, a potent angiogenic inhibitor, can serve as a coating or a co-injectate. Alternatively, it may be desirable for the sheath to be coated with a tissue adhesive, such as Dermabond™, available from Ethicon/Johnson and Johnson, Inc.; or Focalseal™, available from Focal, Inc. to decrease the motion of the tissue implant device relative to the tissue. This is important since relative motion can prevent proper healing and anchoring of the device to the tissue which could eventuate in erosion. In one embodiment, the sheath is constructed of expanded polytetrafluoroethylene coated with fibrin glue containing fibroblast growth factor 1 (FGF1) and heparin.

Generally, the means for filling the sheath is provided by one or more substantially tubular structures adapted to be placed within the sheath during filling, and removable after the sheath has been filled to the desired volume. In one embodiment, the filler tube can be replaced in the sheath after its removal. The filler tube can consist of a variety of tubular structures, depending on the need, including a needle, a compliant or non-compliant plastic tube, or a metal hypotube comprised of stainless steel, nitinol, or any of a variety of materials as appropriate in view of the structure of the implant and desired filling protocol. The tube may have a variety of cross sectional profiles including round, oval, and flattened, depending on the clinical need and the shape of the sleeve to be filled.

In one embodiment, the tissue filling device is constructed and used as follows. The sheath has a proximal end and a distal end. A guide rail, which has a distal end and a proximal end, is adapted so that its distal end extends beyond the distal end of the sheath, then extends through and within the sheath from distal end to proximal end, and then emerges from the proximal end of the sheath such that the proximal end of the guide rail is proximal to the proximal end of the sheath. The guide rail is of small diameter, preferably 0.1-1.0 mm, and can consist of any appropriate filamentous material such as absorbable or non-absorbable suture, a metal such as stainless steel or nitinol, or any material or combination of materials adapted to allow a filler tube to slide over the guide rail and into the interior of the sheath. The guide rail may be coated with a material such as a hydrogel, silicone, ePTFE or PTFE to increase its lubricity.

A sew through method of implanting the tissue filling device is as follows. A sewing needle is attached to the distal end of the guide rail using any of a number of methods as are well known in the art. The sewing needle can be straight or curved, and of small diameter, preferably 0.1-1.0 mm. Where the guide rail engages the distal end of the sleeve, the sleeve is substantially bonded to the guide rail such that filler material cannot escape from the distal end of the sleeve. The guide rail then remains unattached to the sleeve. The filler tube and attached syringe is adapted to ride over the guide rail in order for the filler tube to be placed in the sleeve, and removed therefrom after the sleeve has been filled.

In use, the surgeon measures the length of the path he wishes to fill and picks the sleeve assembly of the appropriate length from a kit of such sleeves. The sewing needle is placed by the surgeon into the skin along the path that he wishes to augment, stopping before the distal end of the sleeve emerges from the skin, and taking care that the proximal end of the sleeve is within the tissue. If it is not, the sleeve may be pulled all the way through the tissue from the distal end, thus removing it completely from the tissue. In this case, the surgeon may chose a sleeve of a different length, or may chose to enter the tissue with the sewing needle at a more proximal location, so that the entire sleeve ultimately lies within the tissue. The surgeon may put manual traction on the tissue in order to guide the needle along the desired path. The filler tube is advanced along the guide rail into the interior of the sleeve until the distal end of the filler tube is located at or near the distal end of the sleeve. A syringe with filler material is slid over the guide rail and attached to the proximal end of the filler tube. The surgeon then ejects filler material into the filler tube and thence into the sleeve. He can withdraw the filler tube along the length of the sleeve until an adequate tissue augmentation profile is achieved. The filler tube is then removed from the sleeve along the guide rail, allowing the valve at the proximal end of the sleeve to close. If more augmentation is desired, the filler tube may be again passed over the guide rail, through the valve and into the sleeve, where more filler material may be deposited. When the desired amount of filler material is within the sleeve, the filler tube is removed and the guide rail is cut flush with the skin at the proximal and distal ends of the sleeve. That portion of the guide rail within the sleeve remains there after the distal and proximal ends are cut.

In an alternative embodiment, one or more stay sutures may also be attached to the proximal end of the sleeve. In use, the stay suture extends from the proximal end of the sleeve and out to the external aspect of the tissue. The surgeon may then grasp these stay sutures to provide counterforce as the filler tube is advance. In addition, the surgeon may grasp the stay sutures and the distal suture, or distal stay sutures if such are provided, in order to move the tissue filling device back and forth within the tissue to achieve optimal positioning. When the desired amount of filler material is within the sleeve, the guide rail is cut flush with the skin at the proximal and distal ends of the sleeve, and the stay sutures are similarly cut close to the skin at the proximal end. The stay and guide sutures are ideally of bioresorbable material as are well known in the art.

In an alternative embodiment and method of use, the tissue filling device is implanted in the tissue to be augmented by means of an outer needle or cannula. The needle has a proximal end and a distal end, and a lumen extending from one end to the other. In one embodiment, the needle is 14-20 gauge. A sleeve assembly consists of the collapsed sleeve, valve and filler tube as described above. Optionally, a central guide rail may be supplied. The sleeve assembly is contained within the needle lumen such that the distal end of the sleeve assembly ends proximally of the distal end of the needle lumen. The filler tube runs through the sleeve and emerges at the proximal end of the needle, and then connected to a syringe containing the filler material. If a central guide rail is provided, the filler tube is adapted to ride over said rail. The filler material can be any of those previously described. In one embodiment, stay sutures are provided attached to the proximal end of the sleeve and emerge through the proximal end of the needle. In use, the surgeon advances the needle along the path in the tissue to be augmented from a proximally located entry site. The surgeon may put manual traction on the tissue in order to guide the needle along the desired path. The filler tube is advanced within the interior of the sleeve, and along the guide rail of such is provide, until the distal end of the filler tube is located at or near the distal end of the sleeve. The needle may be advanced through the tissue and then emerge from the skin at a distally located exit site, or the needle advancement may stop within the tissue without an exit site. In either case, once the needle is in the desired position, forward tension is placed on the filler tube to keep the collapsed sleeve in position, while the needle is retracted proximally out of the tissue. The surgeon then ejects filler material into the filler tube and thence into the sleeve. He can withdraw the filler tube along the length of the sleeve until an adequate tissue augmentation profile is achieved and may re-advance the filler tube distally if required. The filler tube is then removed from the sleeve, allowing the valve at the proximal end of the sleeve to close. If more augmentation is desired, the filler tube may be again passed through the valve and into the sleeve, and over the guide rail if one is provide, where more filler material may be deposited. When the desired amount of filler material is within the sleeve, the filler tube is removed and any guide rail and any stay sutures are cut flush with the skin at the proximal and distal ends of the sleeve.

In one embodiment, the sleeve may take the shape of the upper lip in a "cupids bow" configuration, with the valve and filler tube assembly as provide above. The sleeve of this upper lip shape is also configurable from a first, collapsed state, to an expanded state. The sleeve of this upper lip shape may be placed within the tissue either using the sew-through method or the outer needle method described above. In this embodiment, the sleeve is generally 3 to 6 cm in length, 1 to 6 mm in width and 1 to 3 mm in depth. The upper edge has a flat "M" configuration to match the upper vermillion border of the lip. The sleeve may be constructed of two sheets of any of the biocompatible materials describe above, preferably ePTFE, attached to each other, such as by an adhesive of thermal cintering, along their edges.

In another embodiment, the sleeve is adapted to be placed in the cheek to enhance the malar fossa. In this embodiment, the shape and dimensions are well known in the art, such as described for silicone implants available from McGhan Medical Corporation, a division of Inamed. In one preferred embodiment, the sleeve is approximately ovoid and constructed of two sheets of ePTFE sintered together at their outer edges, such that the sleeve, when in its inflated state, has dimensions of 4 to 6 cm in length, 3 to 4 cm in width, and 0.3 to 1.5 cm in thickness in the center of the sleeve, with the thickness tapering towards the edges.

In another embodiment, the sleeve adapted to be placed in the cheek has the dimensions described above, but additionally contains a length of Nitinol wire or ribbon in its superelastic state, of approximately 0.003 to 0.030 inches in diameter, which is affixed within the edges along the circumference of the sleeve between the sheets of ePTFE, which make up the sleeve, using a thermoplastic adhesive such as FEP or polyethylene. In such an embodiment, the sleeve is assisted in expanding from its first configuration to its second configuration, and maintaining its shape in the second configuration, by the shape memory properties of the Nitinol.

In similar fashion, other embodiments of a sleeve in the size and shape adapted to be used as tissue augmentation implants in the dorsum of the nose, the chin, the region under the eyes, the breast, or any anatomic location clinically indicated may be constructed in the fashion described above either without or with the support of a Nitinol frame structure.

Certain specific implementations of the invention will be described with reference to FIGS. 1-12. Referring to FIG. 1, there is illustrated a schematic representation of a tissue augmentation implant in accordance with one aspect of the present invention. The implant comprises a sleeve 10, having a proximal end 12 and a distal end 14. Sleeve 10 may be either an empty sleeve with a single or plurality of macro compartments, or the outer surface of an open cell or closed cell foam as has been disclosed elsewhere herein.

The sleeve 10 comprises a body 16, which, in the present embodiment, defines a central cavity 18. The body 16 is additionally provided with a distal port 20, which is in communication with a proximal port 22 by way of a lumen extending therebetween. In the illustrated embodiment, the distal port 20 is on a distal end of the body 16 and the proximal port 22 is on the proximal end of the body 16. However, either port may be positioned along the length of the body 16 spaced apart from the respected end, depending upon desired performance and other design considerations. A plurality of ports may also be desirable.

In the illustrated embodiment, the distal port 20 and proximal port 22 serve as guidewire access ports to allow the body 16 to be slideably advanced along a guidewire 24.

The illustrated ports 20 and 22 are in communication with each other by way of the central cavity 18. However, a separate lumen may be provided through the sleeve wall or on the outside of the sleeve if it is desired to isolate the guidewire lumen from the filler media.

As has been discussed herein, the body 16 is transformable from a reduced cross sectional configuration such as for positioning at a desired treatment site, to an enlarged cross sectional configuration for providing a desired cosmetic result. In one embodiment, illustrated schematically in FIG. 2, the body 16 is transformed to the enlarged cross sectional configuration by filling the central cavity 18 with any of a variety of desired filler materials 30. A filler tube 26 is advanced along the guidewire 24 to position a fill port 28 within a desired portion of the central cavity 18. The proximal end of the filler tube 26 (not illustrated) is connected to a source of filler media, such as a hypodermic needle syringe or other container depending upon the nature of the filler media. Suitable filler materials are disclosed elsewhere herein, and the nature of the filler tube may be modified to take into account the nature of the filler as will be apparent to those of skill in the art in view of the disclosure herein.

The filler tube 26 may be advanced throughout the length of the sleeve 10 into the vicinity of the distal end 14. Filler 30 may be deployed through the fill port 28 by activation of a fill control (not illustrated) on the proximal control. The filler tube 26 may be axially proximally retracted through the sleeve 10 to introduce filler 30 at different positions along the length of the sleeve. After a sufficient amount and desired distribution of filler 30 has been introduced into the sleeve 10 to achieve the desired result, the filler tube 26 may be proximally retracted from the proximal end 12, and removed from the patient. See FIG. 3. Proximal end 12 may be provided with a valve 32 as has been described herein, to permit removal of the filler tube 26 and retention of the filler media 30 within the sleeve 10. The guidewire 24 may also thereafter be proximally withdrawn from the sleeve 10, thereby leaving the filled implant in position at the desired treatment site.

For certain applications, the sleeve 10 is preferably fillable to a non-uniform profile. This may be accomplished utilizing the embodiment of FIGS. 1-3, together with a filler which has sufficient viscosity, or structural characteristics (e.g. wire coils) that the filler will remain at a localized position within the sleeve 10. Alternatively, referring to FIG. 4, there is illustrated a segmented embodiment of the invention. The sleeve 10 is divided into a plurality of segments 34, which are separated by a plurality of neck portions 36. The fill port 28 on the fill tube 26 may be sequentially positioned within each of the segments 34, to allow each segment 34 to be inflated to a unique cross sectional dimension. In this manner, the cross sectional dimensions of the implant are customizable along the length of the implant as may be desired to achieve a desired cosmetic result.

The neck portion 36 may be formed in any of a variety of ways, such as by heat forming the sleeve 10, or by placing any of a variety of structures such as a band around the neck portion 36. Referring to FIG. 5, the segmented implant is illustrated with a filler tube 26 in place within a segment 34. Adjacent segments 34 are separated by a restriction 37 such as an annular elastic band or gasket. The restriction 37 has sufficient elasticity to permit passage of the filler tube 26, but recoils back to close of substantially close the passageway between adjacent segments 34 following removal of the filler tube 26. Thus, the restriction 37 may be configured to either restrict and control flow between adjacent segments 34, or completely block flow of filler 30 between adjacent segments 34.

The nature of the restriction 37 in neck portion 36 is configured to cooperate with the nature of the filler 30 as will be appreciated by those of skill in the art in view of the disclosure herein. For example, the restriction 37 need not provide a rigorous seal if the filler 30 comprises a plurality of coils, fibers, or particular material. However, if a less viscous or more flowable filler 30 such as saline solution is utilized, restriction 37 should be configured to provide a seal between segments 34 if it is desired to prevent flow of filler 30 between adjacent segments 34. Optimization of these parameters may be achieved through routine experimentation by those of skill in the art, taking into account the desired clinical performance of the implanted device.

Referring to FIG. 5, a sleeve having a plurality of internal baffles 40 is disclosed. Baffles 40 function to divide the interior cavity 18 of the sleeve 10 into a plurality of chambers or compartments 38, without necessarily influencing the external profile of the implant. Similar to the restriction 37, baffles 40 permit the filler tube to be advanced and retracted to reach each compartment 38, and then to prevent or to substantially prevent the flow of filler 30 between adjacent compartments depending upon the desired clinical performance. As a further alternative, the baffles 40 or valves may be in the form of a pierceable septum, which permits passage of the fill tube 26 but which reseals either completely or substantially following removal of the filler tube 26.

Figure 7:
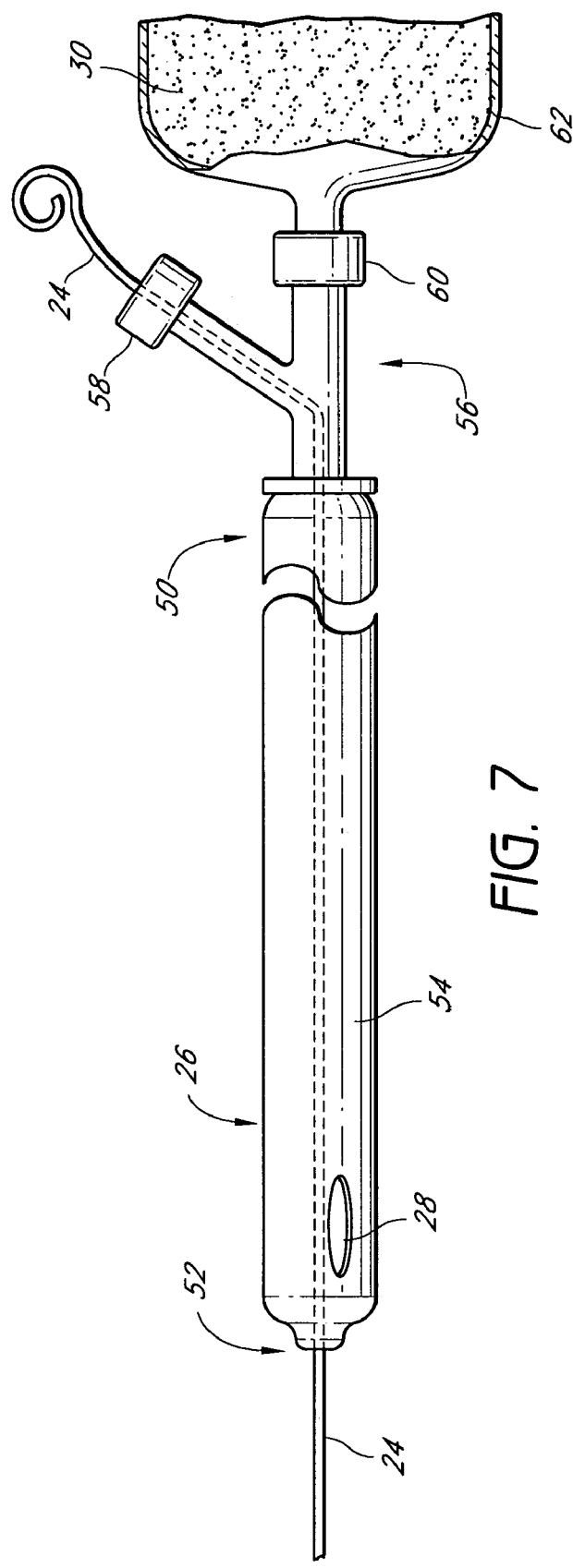
FIG. 7 is a side elevational schematic view of a filler tube in accordance with the present invention.

Referring to FIG. 7, there is illustrated one embodiment of a filler tube 26 in additional detail. Filler tube 26 comprises a proximal end 50, a distal end 52 and an elongate tubular body 54 extending therebetween. Tubular body 54 may be flexible or rigid, depending upon the desired performance. Tubular body 54 may be formed in any of a variety of ways, such as by machining from metal components (e.g. stainless steel hypotube) or by extruding any of a variety of polymeric materials well know in the catheter arts, such as PEEK, PEBAX, various densities of polyethylene, among others.

The tubular body 54 includes at least one central lumen for receiving the guidewire or guide rail 24 therethrough. The guidewire lumen is in communication with a guidewire access port 58 on the proximal manifold 56. Proximal manifold 56 is additionally provided with a filler port 60, which may be a lure connector or other quick release hub, for removable connection to a source 62 of filler 30. In one convenient embodiment, source 62 is in the form of a manually activatable syringe.

The tubular body 54 may be provided as a dual lumen structure, having either concentric or side-by-side lumens as is well known in the catheter arts. Alternatively, depending upon the nature of the filler 30, the guide rail 24 may extend through the same lumen as the filler media as well be appreciated by those of skill in the art in view of the disclosure herein.

Although the filler tube 26 is illustrated as having a single effluent port 28 for introducing filler 30 into the sleeve 10, a plurality of filler ports 28 may be provided. In addition, the filler port 28 may be the same as the distal opening through which the guide rail 24 extends. In an embodiment having multiple effluent ports 28, the multiple ports may be arrange circumferentially in a single transverse plane about the tubular body 54, or may be spaced axially apart along the length of the tubular body 54 such as for use in a procedure where it is desired to fill multiple compartments 38 simultaneously.

Figure 8:
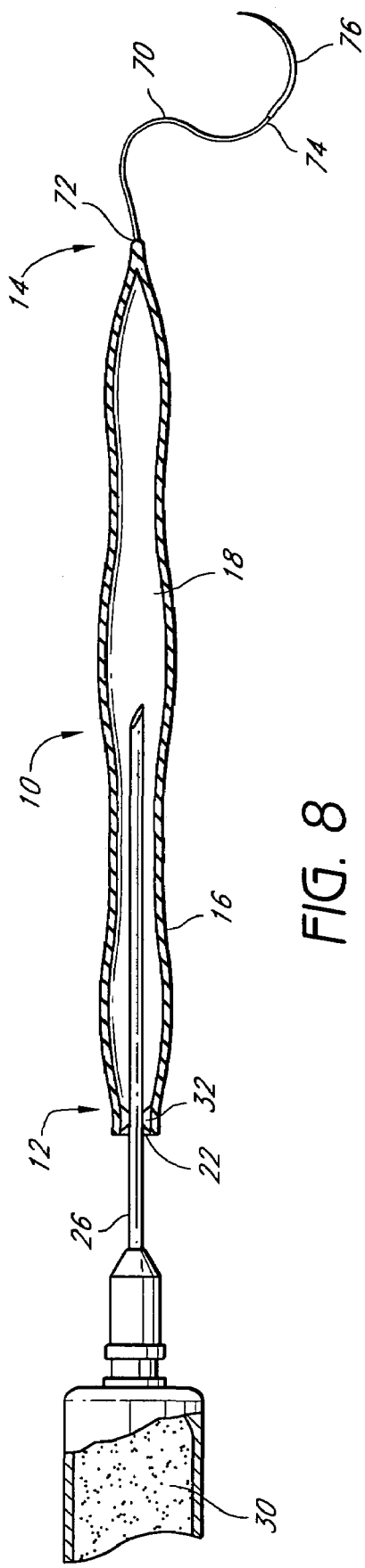
FIG. 8 is a side elevational view of an implant removably attached to a filler tube.

A further implementation of the invention is illustrated in FIG. 8. A schematically illustrated sleeve 10 extends from a proximal end 12 to a distal end 14. The sleeve comprises a flexible body 16 which may comprise an outer fabric sleeve or the outer surface of a segment of foam, as has been discussed elsewhere herein. In the illustrated embodiment, the body 16 defines at least one central cavity 18, having a proximal port 22. Proximal port 22 is provided with a valve 32, for sealing the central cavity 18 following introduction of filler material 30 and removal of the filler tube 26.

In the implementation of the invention illustrated in FIG. 8, the distal end 14 of the sleeve 10 is provided with a closed end. A distal suture 70, extending from a proximal end 72 to a distal end 74 is attached to the closed distal end 14 of the sleeve 10. In alternative embodiments, distal end 14 may be provided with an open access port, with or without a valve, depending upon the desired filling configuration. The suture 70 may also extend throughout the length of the sleeve 10, and proximally from the proximal end 12 of sleeve 10, depending upon the desired performance.

In the illustrated embodiment, the distal suture 70 extends from the distal end 14 of the sleeve 10, to a needle 76 attached to the distal end 74 of the suture 70. Needle 76 may comprise any of a variety of sewing needles, as will be apparent to those of skill in the art in view of the disclosure herein.

Figure 9:
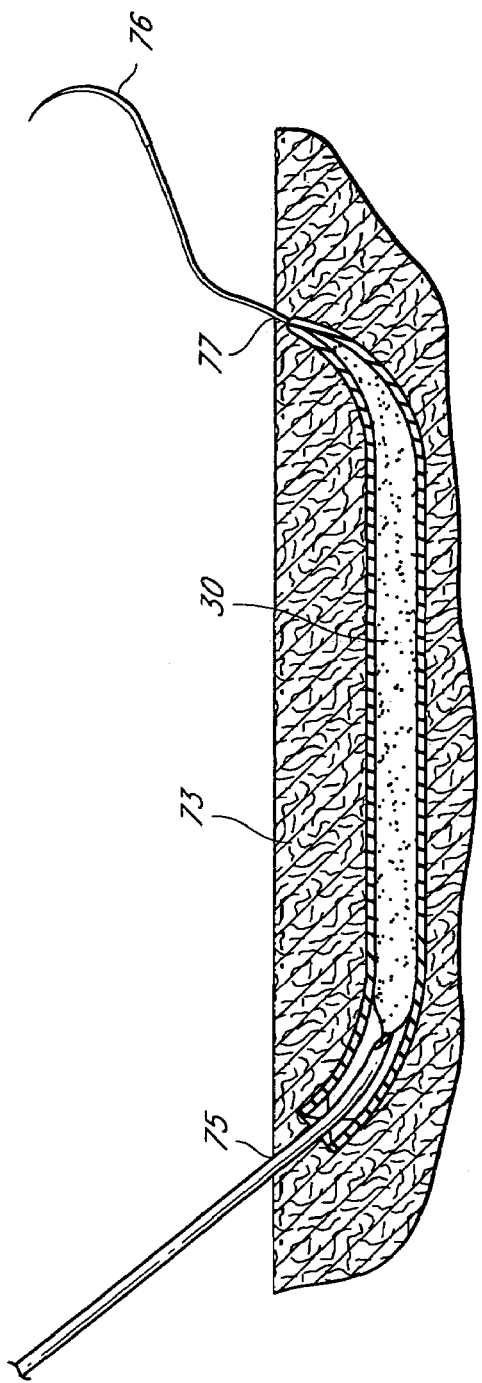
FIG. 9 is a side elevational schematic view of the implant of FIG. 8, positioned beneath the skin.

FIG. 9 schematically illustrates the use of the embodiment of FIG. 8. The needle 76 is introduced into the skin 73 at a first access point 75. The needle is advanced subcutaneously beneath an area to be treated. Needle 76 is thereafter advanced through the surface of the skin at an exit point 77. Further traction on the needle 76 and suture 70 pull the tubular sleeve 10 through the entrance point 75 and into position beneath the region of skin to be treated. Once the sleeve 10 is in the desired position, the filler material 30 is advanced from a source into the central cavity 18. Following introduction of a desired volume of filler material 30, the filler tube 26 is proximally withdrawn from the sleeve 10, and the distal suture 70 is severed at or below the skin surface.

Figure 10:
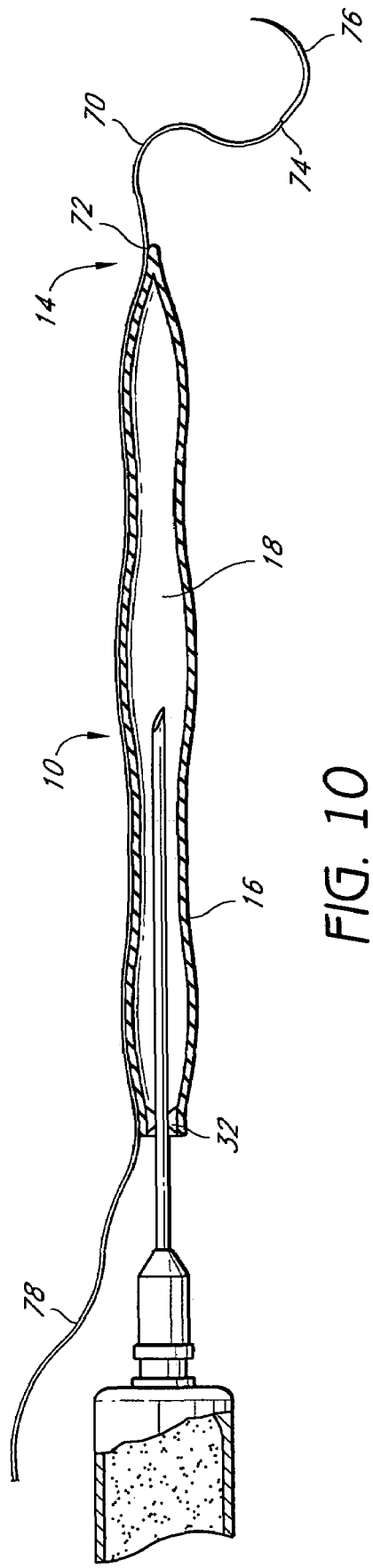
FIG. 10 is a side elevational view of an implant removably attached to a filler tube.
Figure 11:
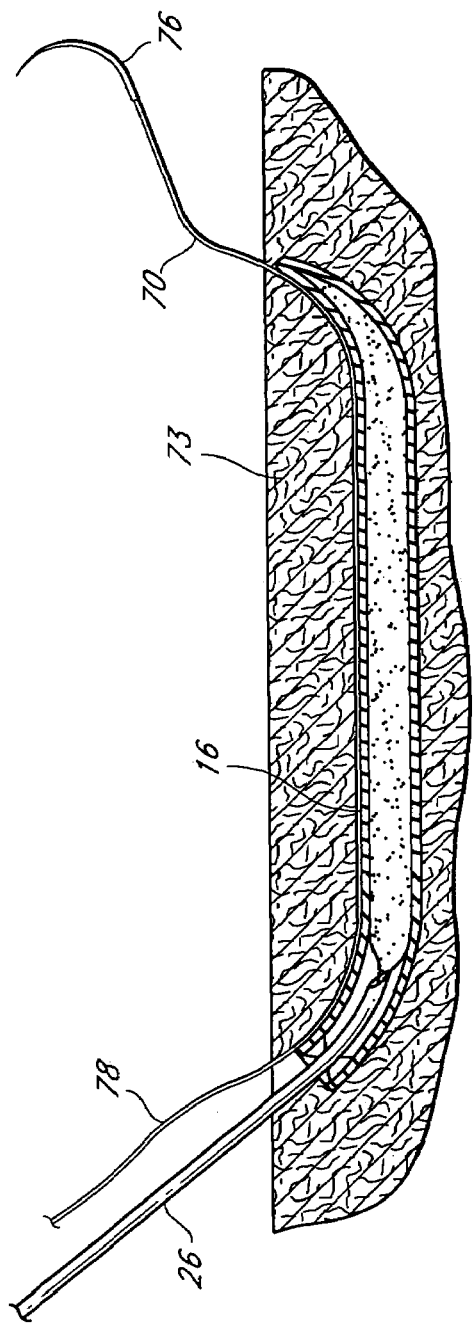
FIG. 11 is a side elevational schematic view of the implant of FIG. 10, positioned beneath the skin.

Referring to FIGS. 10 and 11, there is illustrated an embodiment like that in FIGS. 8 and 9, with the added feature of a proximal stay suture 78. Proximal stay suture 78 may be attached to the sleeve 10 in the vicinity of the valve 32, or may be a continuous suture with the distal suture 70, extending along the outside or the inside of the body 16.

In use, the proximal stay suture 78 and the distal suture 70 may be used to manipulate the sleeve 10 along its axis to optimize positioning either before, during or following introduction of filler material 30 into the central cavity 18.

A schematic representation of the use of an external introduction needle is illustrated in FIG. 12. In the present context, the use of the term "needle" is not intended to imply any specific structural dimensions, other than as necessary to provide access for subcutaneous insertion of the implant. The actual dimensions of the introduction needle will be optimized for or governed by the configuration of the implant and filler tube as will be apparent to those of skill in the art.

Placement needle 82 comprises an elongate tubular body 83 extending between a proximal end 84 and a distal end 86. Tubular body 83 comprises an elongate central lumen 88 extending therethrough. The tubular body 83 may comprise any of a variety of forms, depending upon the intended clinical use. For example, tubular body 83 may comprise a straight, a curved, or a flexible configuration. Typically, the distal end 86 will be provided with a bevel or other sharpened tip, to facilitate advance through soft tissue. Depending upon the diameter of the tubular body 83, a separate obturator tip may be positioned within the tubular body 83 to facilitate positioning of the tubular body 83 in the desired treatment site. The obturator may thereafter be removed, and the sleeve 10 advanced into position within the tube.

In the embodiment schematically illustrated in FIG. 12, the tube 83 has a sufficient inside diameter to accommodate a proximal hub 90 on the filler tube 26. This allows the placement needle 82 to be proximally retracted over the assembly of the sleeve 10 and filler tube 26 following placement at the treatment site. Alternatively, the placement needle 82 can be configured to be withdrawn in a distal direction out of the exit point 77 (see FIG. 9). Thus, depending upon the desired clinical performance, the placement needle 82 may be proximally retracted or distally advanced off of the sleeve 10. In an alternate configuration, placement needle 82 may be in the form of a peel-away sheath, which can be removed proximally without the need for an inside diameter sufficient to accommodate the proximal hub 90. Any of a variety of configurations may be utilized for the placement needle 82, as will be apparent to those of skill in the art in view of the disclosure herein.

Referring to FIGS. 13A through 13D, there is illustrated a manufacturing sequence for a tissue augmentation device in accordance with the present invention. 13A illustrates a tubular sleeve 100 which extends between a proximal end 102 and a distal end 104. A central lumen 106 extends therethrough. Tubular sleeve 100 may comprise any of a variety of materials such as ePTFE and others described elsewhere herein. In general, tubular sleeve will have a sufficient length and diameter to accommodate the desired treatment site. For treatment of wrinkles in the face, tubular sleeve 100 will generally have a length within the range of from about 1 cm to about 6 cm, and a diameter within the range of from about 1 mm to about 8 mm. The wall thickness of the tubular sleeve 100 may also be varied considerably, but will often be within the range of from about 0.003 to about 0.020 inches.

Referring to FIG. 13B, there is illustrated the first step in construction of the proximal valve 114. A biasing element 108 such as an elastic band, suture, spring biased metal clip, or other clamp or biasing member is positioned around the tubular sleeve 100 to create a neck, spaced slightly apart from the proximal end 102 leaving a trailing end 110 of the tube 100. The biasing element 108 is preferably sufficiently tightly positioned around the tube 100 to provide a suitable seal taking into account the desired filler material as has been discussed.

Figure 13C:
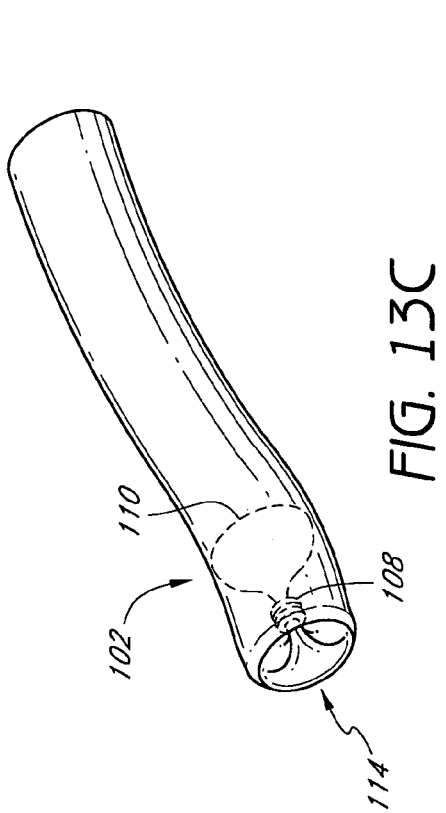

As seen in FIG. 13C, the tubular body 100 is then turned inside out (everted) so that the trailing end 110 is positioned within the central lumen 106. The biasing element 108 is also positioned within the central lumen 106, presenting a valve opening 114 on the proximal end 102 of the tubular body 100. Valve opening 114 permits the introduction and removal of a filler tube as has been discussed.

Figure 13D:
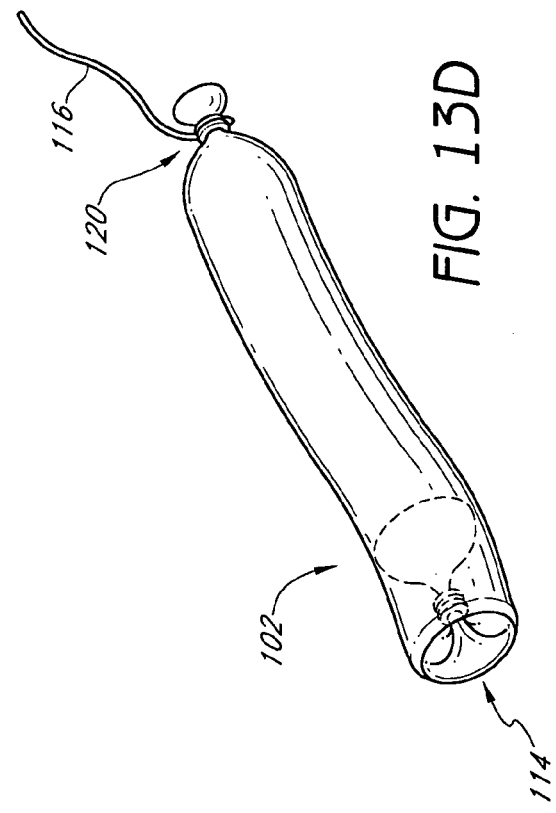

Referring to FIG. 13D, a distal closed end 120 is formed on the tube 100. Closed end 120 may be provided in any of a variety of ways, such as by one or more loops of a suture 118 which may be tied into a knot. Alternatively, any of a variety of adhesives, thermal welding, elastomeric bands, clips or other biasing structures such as those utilized to form valve 114 may be used. In the illustrated embodiment, closed end 120 is provided by tying a suture tightly around the distal end 104 of the tube 100. A trailing end 116 of the suture is left attached to the suture knot, to provide assistance during positioning as has been discussed. The distal suture 116 may thus be provided with a sewing needle (not illustrated) for percutaneous introduction into the treatment site.

Figure 14:
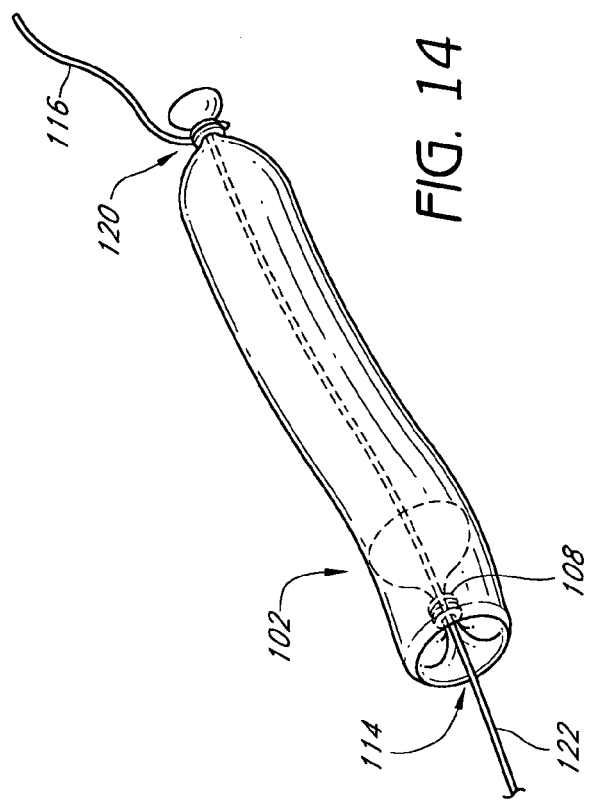
FIG. 14 illustrates a bulking device as in FIG. 13D, additionally showing a guidewire.

Referring to FIG. 14, there is illustrated a tissue augmentation device as in FIG. 13D, with an optional guidewire 122. Guidewire 122 extends through the valve 114, and at least as far as the distal closed end 120. Guidewire 122 may be permanently attached, at the closed distal end 120, or may be removable such as by proximal traction depending upon the desired clinical performance. In one embodiment, the guidewire 122 is secured within the suture knot 118 and not intended for removal. In this embodiment, following placement and filling of the implant, the proximal portion of guidewire 122 is severed at about the valve 114. Guidewire 122 may comprise any of a variety of filaments, such as a suture, or a metal wire such as stainless steel or Nitinol. As has been discussed, guidewire 122 may provide assistance in axial repositioning or positioning of the filler tube, which may be advanced over the guidewire 122 and into the tubular sleeve 100.

Although the present invention has been described in connection with certain specific embodiments, various additional embodiments and alterations to the described embodiments are contemplated within the scope of the invention. Accordingly, the scope of the invention is not intended to be limited by the foregoing, and is intended to extend to the full extent of the attached claims.

What is claimed is:

1. A tissue augmentation device, comprising:
   an elongate, flexible body, having a proximal end and a distal end;
   at least a first port on the proximal end, for accessing the interior of the body;
   a valve for closing the port; and
   a suture extending from the distal end.

2. A tissue augmentation device as in claim 1, further comprising a needle on the suture.

3. A tissue augmentation device as in claim 1, wherein the body comprises a tubular sleeve.

4. A tissue augmentation device as in claim 1, wherein the body comprises a sleeve with a flattened cross section.

5. A tissue augmentation device as in claim 1, wherein the body comprises a sleeve composed of two sheets of material bound together along their periphery.

6. A tissue augmentation device as in claim 1, wherein the body comprises two concentric tubular layers.

7. A tissue augmentation device as in claim 1, further comprising a second port for accessing the interior of the body.

8. A tissue augmentation device as in claim 1, further comprising at least two compartments within the flexible body.

9. A kit, for augmenting tissue, comprising:
   at least one elongate, flexible body, which is transformable from a first configuration for implantation to a second configuration for augmentation;
   a valve on the body;
   at least one suture attached to the body;
   a filler tube for permitting access to the interior of the body; and
   a filler, for transforming the body from the first configuration to the second configuration.

10. A kit as in claim 9, wherein the body comprises a tubular sleeve.

11. A kit as in claim 9, wherein the body comprises a plurality of internal compartments.

12. A kit as in claim 9, comprising at least a second suture attached to the body.

13. A kit as in claim 9, wherein the filler comprises a liquid.

14. A kit as in claim 9, wherein the filler is polymerizable in situ.

15. A kit as in claim 9, further comprising a syringe for injecting the filler into the filler tube.

16. A kit, for augmenting tissue, comprising:
   a plurality of elongate, flexible bodies, each of which is transformable from a first configuration for implantation to a second configuration for augmentation, provided in a plurality of sizes and shapes.

at least one suture attached to each body;

a filler tube for permitting access to the interior of the body; and at least two different fillers, for transforming the body from the first configuration to the second configuration.

17. A kit as in claim 16, wherein the fillers have different viscosities.

18. A kit as in claim 16, wherein the fillers have different durometers.

19. A kit, for augmenting tissue, comprising:

at least one elongate, flexible body, which is transformable from a first configuration for implantation to a second configuration for augmentation;

at least a first and a second suture attached to the body;

a filler tube for permitting access to the interior of the body; and a filler, for transforming the body from the first configuration to the second configuration.

20. A kit as in claim 19, wherein the body comprises a tubular sleeve.

21. A kit as in claim 19, wherein the body comprises a plurality of internal compartments.

22. A kit as in claim 19, wherein the body comprises a valve.

23. A kit as in claim 19, wherein the filler comprises a liquid.

24. A kit as in claim 19, wherein the filler is polymerizable in situ.

25. A kit as in claim 19, further comprising a syringe for injecting the filler into the filler tube.

26. A kit, for augmenting tissue, comprising:

at least one elongate, flexible body, which is transformable from a first configuration for implantation to a second configuration for augmentation;

at least one suture attached to the body;

a filler tube for permitting access to the interior of the body; and a filler, for transforming the body from the first configuration to the second configuration;

wherein the filler is polymerizable in situ.

27. A kit as in claim 26, wherein the body comprises a tubular sleeve.

28. A kit as in claim 26, wherein the body comprises a plurality of internal compartments.

29. A kit as in claim 26, wherein the body comprises a valve.

30. A kit as in claim 26, comprising at least a second suture attached to the body.

31. A kit as in claim 26, wherein the filler comprises a liquid.

32. A kit as in claim 26, further comprising a syringe for injecting the filler into the filler tube.

* * * * *

UNITED STATES PATENT AND TRADEMARK OFFICE
CERTIFICATE OF CORRECTION

PATENT NO.       : 7,244,270 B2                                    Page 1 of 1
APPLICATION NO.  : 10/942728
DATED            : July 17, 2007
INVENTOR(S)      : Michael D. Lesh It is certified that error appears in the above-identified patent and that said Letters Patent is hereby corrected as shown below:

In Col. 6, line 64, please delete "HylaforM$^{TM}$," and insert --Hylaform$^{TM}$,-- , therefor.

In Col. 7, line 25, please delete "Victyl" and insert --Vicryl--, therefor.

In Col. 18, line 67, Claim 16, please delete "shapes." and insert --shapes;--, therefor.

Signed and Sealed this

Eleventh Day of December, 2007

JON W. DUDAS
*Director of the United States Patent and Trademark Office*